United States Patent [19]

Piekarski et al.

[11] Patent Number: 5,357,346
[45] Date of Patent: Oct. 18, 1994

[54] SOLDERABILITY TESTER METHODOLOGY

[75] Inventors: Brett Piekarski, College Park; George K. Lucey, Burtonsville, both of Md.; John Langan, Santa Barbara, Calif.

[73] Assignee: The United States of America as represented by the Secretary of the Army, Washington, D.C.

[21] Appl. No.: 980,400

[22] Filed: Nov. 24, 1992

[51] Int. Cl.⁵ .................................... G01N 21/55
[52] U.S. Cl. .................................... 356/448; 356/36
[58] Field of Search .................... 356/448, 36, 445

[56] References Cited

U.S. PATENT DOCUMENTS

| | | | |
|---|---|---|---|
| 3,910,701 | 10/1975 | Henderson et al. | 356/39 |
| 4,511,800 | 4/1985 | Harbeke et al. | 250/372 |
| 4,664,514 | 5/1987 | Corby, Jr. | 356/36 |
| 4,894,552 | 1/1990 | Gassenhuber et al. | 250/572 |

OTHER PUBLICATIONS

C. W. Stanley et al., "Differential Reflectometry . . . Phenomena", *Corrosion Science*, vol. 20, pp. 467–480 (1980).
I. Kawakatsu, "Wettability of Liquid Tin on Solid Copper", *Transactions of the Japan Institute of Metals*, vol. 14, 114–119, (Mar. 1973).
R. J. Day "Chromium Chronate . . . Oxidation," *Surface & Interface Analysis*, vol. 8, pp. 33–36 (1986).
Holbrook et al., "A 'Differential Reflectometer'. . . Reflectivity", *Rev. of Scientific Instruments*, vol. 44(4), pp. 463–466 (1973).
Roos, et al., "Quant. Interface Roughness . . . on Copper", *Thin Solid Films*, vol. 164, pp. 5–11 (1988).
Poling, *Infrared Reflection Studies*, vol. 116, No. 7 pp. 958–963 (1969).

*Primary Examiner*—Vincent P. McGraw
*Attorney, Agent, or Firm*—Saul Elbaum; Freda L. Krosnick

[57] ABSTRACT

A methods for gauging the solderability of printed circuit boards or printed wiring boards using differential reflectometry techniques. The method facilitates the determination of solderability properties of a substrate in a non-destructive manner.

12 Claims, 8 Drawing Sheets

FIG. 1

DIFFERENTIAL REFLECTOGRAMS OBTAINED FOR COPPER WHICH WAS EXPOSED TO A LABORATORY ENVIRONMENT FOR (A) 1 DAY; (B) 4 DAYS AND; (C) 11 DAYS [32]. THE CURVES ARE SHIFTED FOR CLARITY

SOLDERABILITY TESTER METHODOLOGY

GOVERNMENTAL INTEREST

The invention described herein may be manufactured, used and licensed by or for the U.S. Government for governmental purposes without the payment to us of any royalties.

BACKGROUND OF THE INVENTION

Poor solderability of printed wiring boards (PWBs) or printed circuit boards (PCBs) and their associated component leads is a difficulty encountered throughout the U.S. Department of Defense as well as throughout private industry. A primary cause for solderability degradation of PWBs is oxidation of the base metal and/or the oxidation of coatings applied to or present over said base metals. Solderability can be retarded by the presence of oxide films on the base metals or protective coatings. This oxide film may be formed by available and present natural resources, such as small amounts of oxygen in the atmosphere.

Currently, fluxes are used during the soldering process in an attempt to resolve the problem. Fluxes are designed to remove surface oxides and then to protect the surface from reoxidation during subsequent soldering processes. However, it has been found that even after fluxes are employed, highly oxidized base metals or coatings experienced degradation in solderability. Therefore, even when fluxes are employed, some method to pre-gauge a PWB, PCB, or a component lead for solderability is essential.

Currently, tin-lead and some other metallic materials are used as protective coatings to prolong solderability of base materials. A problem, however, arises with the use of metallic protective coatings in that these coatings are subject to oxidation and the growth of intermetallics, both of which can detrimentally effect the solderability properties of a substrate.

Since poor solderability of PWBs and PCBs remains a problem, the invention herein will at a minimum simplify the method of detecting this problem.

Currently, solderability of a PWB is measured by testing coupons attached to the PWB while components are tested by testing their actual leads. This is presently accomplished by applying solder to the coupon or component lead and then examining it for a variety of parameters such as area of spread, dewetting, wetting force and wetting time. For PWBs, this is an indirect test and does not give a true solderability measure of the board itself. For components, it requires the actual application of solder to the leads prior to the actual soldering step. Moreover, these tests tend to be subjective in nature and therefore not very reliable.

Another procedure presently under development for testing and measuring the solderability of a circuit board is a technique called electrochemical reduction. Although this experimental technique does not involve the application of solder onto the component part to be evaluated, it requires the application of a reducing agent to remove surface oxides and physically affects the component part.

The principle of monitoring an oxide coating thickness is the topic of G W. Poling, "Infrared Reflection Studies of the Oxidation of Copper and Iron," *Journal of electrochemical Society*, Vol. 116, No. 7 (July, 1969) and C. W. Shanley, "Differential Reflectometry—A New Optical Technique to Study Corrosion Phenomena," *Corrosion Science*, Vol. 20 (1980). These articles show a direct relationship between the intensity of the reflectance spectra of copper and the thickness of cuprous and cupric oxide on the copper surface. This teaching additionally supports the axiom that the reflectance of, for example, a printed circuit board can be used to monitor the oxide thickness present. It nowhere, however, teaches the use of reflectance to measure solderability qualities of a substrate.

As set forth above, the existing solderability testing techniques have their limitations. The present invention, the method of gauging solderability, does not have any adverse limitations on its operability. The present methodology for gauging solderability is a procedure that may be used on various base metals and coatings in conjunction with various solders. It does not involve the application of any solder and does not physically alter the component to be evaluated. Moreover, the present invention tests the component directly and does not require the use of test coupons. Use of the present invention facilitates the thorough, expeditious and efficient inspection of the solderability property of printed circuit boards.

To date, a method of directly determining the solderability of a circuit board which has no adverse or physical affect to the component board itself has not been proposed.

BRIEF SUMMARY OF THE INVENTION

The present invention is directed to a methodology for gauging the solderability of, for example, printed wiring boards. It is a method which may be exercised on a variety of base metals and coatings; it does not involve the application of solder onto said base component or coating; it does not physically affect the component; it eliminates the need for the use of test coupons; and it allows for a thorough and quick inspection of the component for its solderability qualities.

The method of the present invention utilizes differential reflectometry techniques to determine the oxide thickness on the component to be evaluated. In addition, the present invention makes use of the correlation between the oxide thickness present and the solderability of the component base material or coating in order to gauge the component's solderability in terms of its reflectance. To dater this technique has not been used to determine and evaluate solderability properties. This method of evaluating the solderability properties of a circuit board, for instance, has never been suggested.

Accordingly it is an object of the present invention to provide an improved method for evaluating the solderability properties of a component board, such as a printed wiring board.

It is further an object of the present invention to provide a method of testing solderability, wherein said method does not involve the application of solder to the component to be tested.

Another object of the invention is to provide a method for testing the solderability of a circuit board wherein said method does not physically alter or affect the circuit board.

Still another object of the present invention is to provide a method for testing the solderability of a device, wherein said method eliminates the use of test coupons.

Still a further object of the present invention is to provide a thorough, expeditious and efficient method for testing the solderability properties of a base metal or coatings thereon.

Other objectives and features of the present invention will be apparent from the following detailed description of the invention and claims.

DETAILED DESCRIPTION OF THE INVENTION

The invention herein is a method for evaluating, predicting and testing the solderability characteristics of base metals or coatings, for instance in printed wiring boards (PWBs) or printed circuit boards (PCBs).

The method within the scope of the present invention makes use of conventional differential reflectometry. Differential reflectometry is a form of modulation spectroscopy which measures the normalized difference in reflectivity between two samples, or two adjacent areas of the same sample. A conventional differential reflectometer of the type which may be employed herein is described and depicted in C. W. Shanley et al., "Differential Reflectometry—A New Optical Technique to Study Corrosion Phenomena," *Corrosion Science*, Vol. 20, pp. 467–480 (1980).

The process of differential reflectometry has been used to determine oxide thickness and oxide type. This process, however, has been applied primarily in corrosion studies. It has not been applied in any manner to predict or evaluate solderability.

The invention herein makes use of an already established correlation between measurable oxide thickness and solderability. The correlation between oxide thickness and solderability has been shown and evaluated in the past for various metals and coatings, an example of which is depicted in Ichiro Kawakatsu, "Wettability of Liquid Tin on Solid Copper," *Transactions of the Japan Institute of Metals*, Vol. 14, pp. 114–119 (March, 1973). The oxide thickness on a component substrate, as already stated, does have a well established relationship to the reflectance of the substrate. Hence, taken a step further, since reflectance and oxide thickness have in the past been associated with one another, and since this invention uses the documented correlation between oxide thickness and solderability, reflectance can then be directly correlated to solderability properties. To date, this correlation is nowhere suggested in the prior art teachings. This invention will provide a means using the relationship between reflectance and oxide thickness and the relationship between oxide thickness and solderability to gauge and evaluate the solderability properties of various substrates, such as printed circuit boards or printed wiring boards.

In the present invention, the solderability properties are evaluated using the following parameters: differential reflectivity measurement, index of refraction, index of absorption and correlation between oxide thickness and solderability or by directly correlating the differential reflectivity measurement and solderability. It is this method of evaluating solderability that is novel. To date, there is no solderability test available that correlates reflectance and solderability, wherein said method can be conducted in a manner which is non-destructive to the evaluated sample.

A novel approach for protecting, for example, a copper printed circuit board is to apply a chromate conversion coating over the base metal. The application of chromate coatings are already within the skill of the art as having been used to protect copper pads on printed wiring board applications. The advantage of applying a chromate coating to a printed wiring board or printed circuit board to prolong their solderability is that any initial oxidation which may have occurred on the copper board is etched away during the application of the chromate coating. Moreover, the possibility of the formation of copper-tin intermetallics is eliminated by the use of said protective coating. An additional benefit realized from using the chromate coating is that said coating is easily and readily removed from the substrate during the soldering process.

Use of a chromate protective coating, however, only slows down the oxidation process which has substantial affects on the solderability properties of a base metal. Therefore, solderability testing methods are still very much in need. Since copper can diffuse through the chromate coating and form oxides on its surface as depicted in Robert J. Day, "Chromium Chromate as an Inert Marker in Copper Oxidation," *Surface and Interface Analysis*, Vol. 8, pp. 33–36 (1986), the use of chromate coated copper substrates can easily be referred to demonstrate the present invention.

The solderability tester herein uses a conventional differential reflectometer. An unpolarized white light source may be used to produce wavelengths of 200 to 800 nm. The emitted light is passed through various components of the differential reflectometer. For example purposes, the unpolarized white light passes through a monochromator and onto a set of mirrors which reflect the light onto the sample component to be analyzed. The light is then reflected off of the sample through another set of mirrors and to a photomultiplier. The photomultiplier then provides an electronic signal which is then processed in a conventional fashion to calculate the change in reflectance (dR) and the average reflectance ($R_a$) between the sample and a predetermined reference standard. This process will be described further in the detailed description of the drawings.

The reference standard, which is chosen to accommodate the material to be evaluated using the present invention, is of the same material which is being evaluated as the sample component. This reference material will either have no oxide layer present on its surface or it will have a known amount of oxide present.

Data is then plotted for the ratio of the change in reflectance (dR) and the average reflectance ($R_a$) between the test sample and the reference sample over a set range of light wavelengths, for example 200–800 nm. A plot of this data will permit one having ordinary skill in the art to identify the type of oxide(s) present on the surface of the test sample (note, for example, the peak for cuprous oxide on copper at 380 nm, see FIG. 1 of the drawings). Moreover, by determining the peak height of the $dR/R_a$ plot at a given wavelength and using the index of refraction and the index of absorption, the thickness of the oxide layer can be determined by using the reflectivity equations for layered materials. Once the thickness of and the type of oxide is determined, this data is compared against empirical data which correlates the oxide thickness to the solderability. Or, one can directly correlate the value of the $dR/R_a$ plot at a given wavelength to the solderability of the sample.

Obtaining and evaluating the above-identified differential reflectance figures allows one to easily determine the solderability of the component inspected. The present procedure is a passive, non-destructive means for measuring and evaluating solderability properties of various component surfaces.

The types of components which may be evaluated for their solderability properties are components such as printed circuit boards, printed wiring boards, and similar devices. These components may be composed of various conventional base materials or coatings such as copper, nickel, palladium, tin, and solder.

As set forth above, the present invention merely provides for a method of testing the solderability of various substrates. It makes use of the well-known relationship between reflectance and oxide thickness, as well as the relationship between oxide thickness and wettability. Since the solderability of, for example a printed circuit board is dependent upon the coating and particularly the oxide thickness, reflectance measurements of said PCB can be used to passively (non-destructively) gauge the solderability of the PCB. To date, this relationship of reflectance and solderability have not been employed to evaluate solderability properties.

For a further explanation of the invention, reference should be made to the discussion below with regard to the accompanying drawings and the embodiment disclosed.

BRIEF DESCRIPTION OF THE DRAWINGS

The present invention will be described with reference to the accompanying figures and drawings.

DETAILED DESCRIPTION OF THE DRAWINGS

Figure 1:
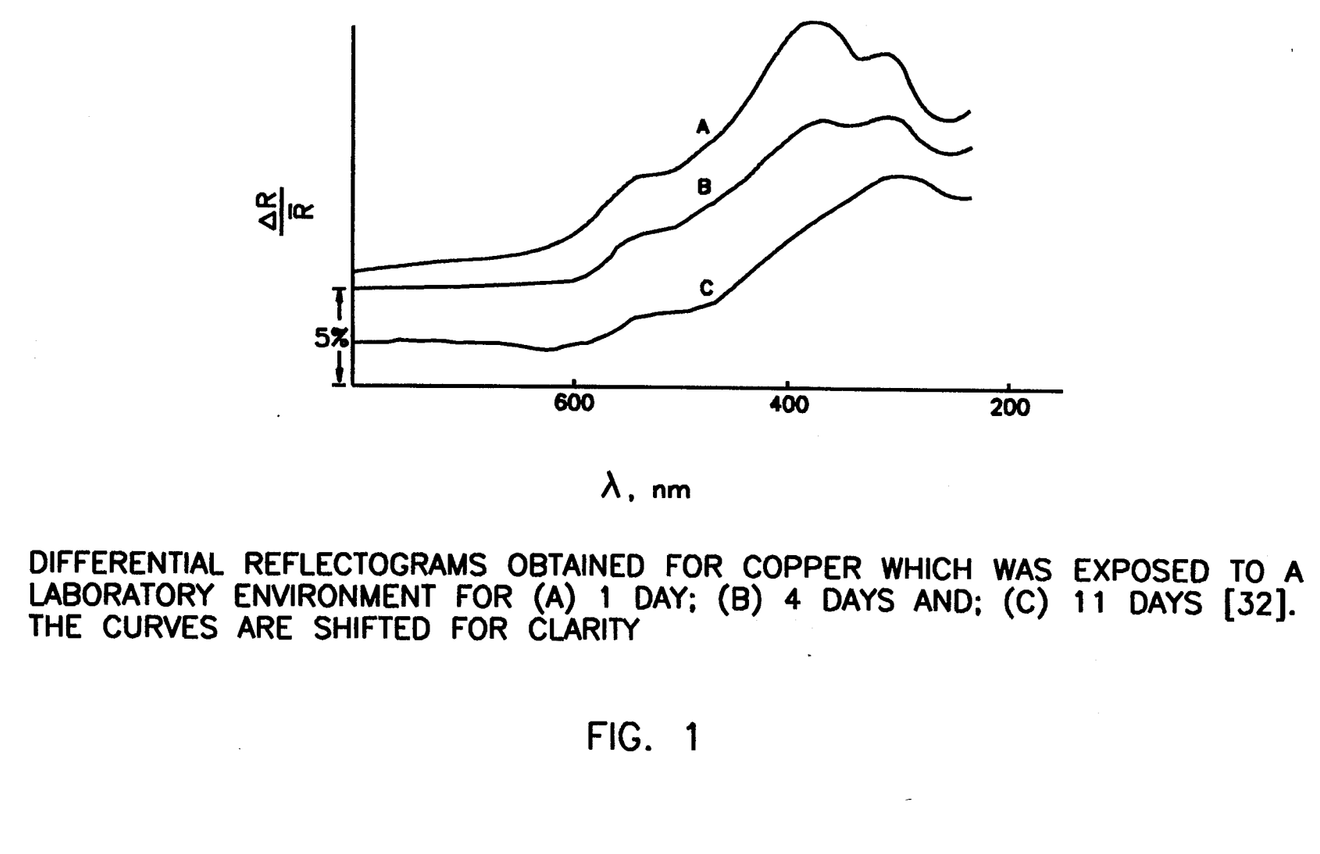
FIG. 1 is a differential reflectivity plot ($dR/R_a$ vs. wavelength) of an aged sample of pure copper. See, C. W. Shanley, "Differential Reflectometry—A New Optical Technique to Study Corrosion Phenomena," *Corrosion Science*, Vol. 20 (1980).

FIG. 1 is a differential reflectivity diagram for an aged sample of pure copper. It shows the characteristic peaks that are caused by the growth of $Cu_2O$.

Figure 2:
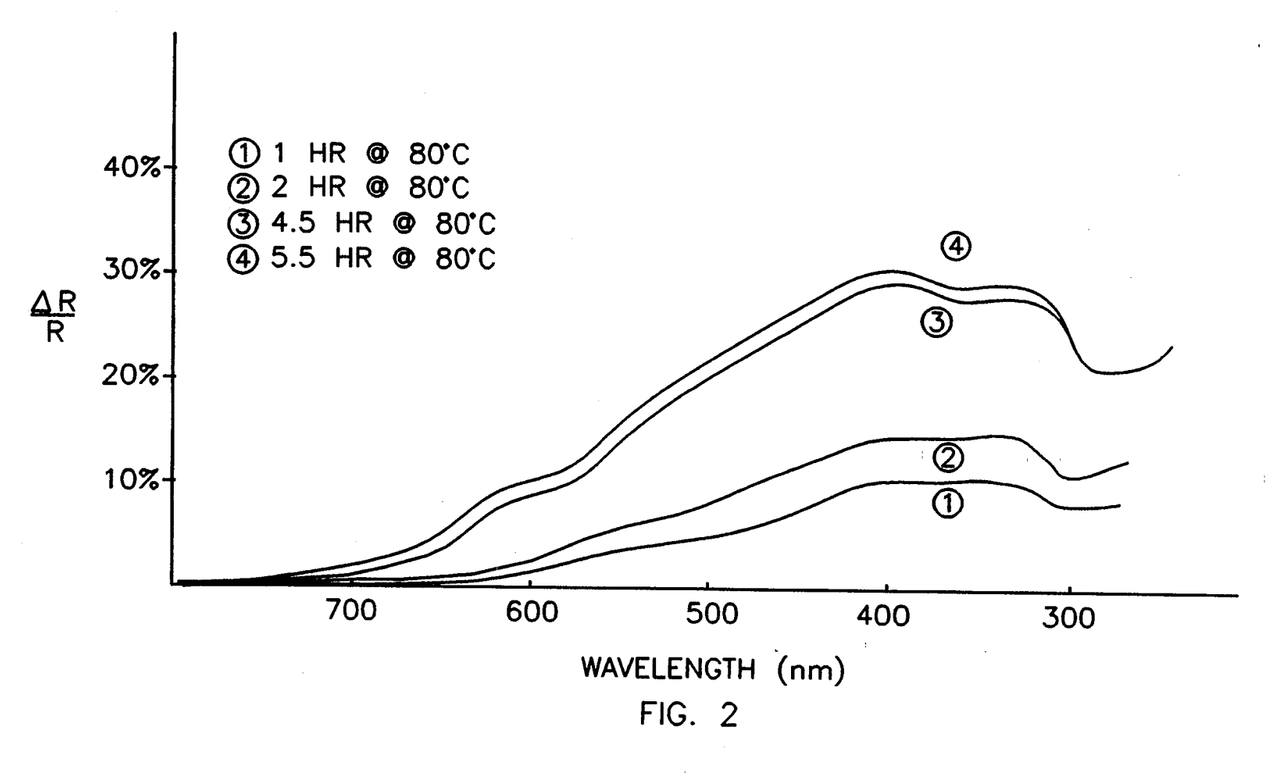
FIG. 2 is a differential reflectivity plot of a successively aged chromate coated copper sample (experimental data).

FIG. 2 is a sequential differential reflectivity diagram of a chromate coated PWB sample. It shows the differential reflectivity plot of a single sample after various aging times. The location of the peaks identify the oxide as $Cu_2O$ and the increasing heights of the peaks indicate an increasing oxide layer. From FIGS. 1 and 2, it is obvious that even though a chromate coating was applied to the copper surface, copper oxides were still formed.

Figure 3:
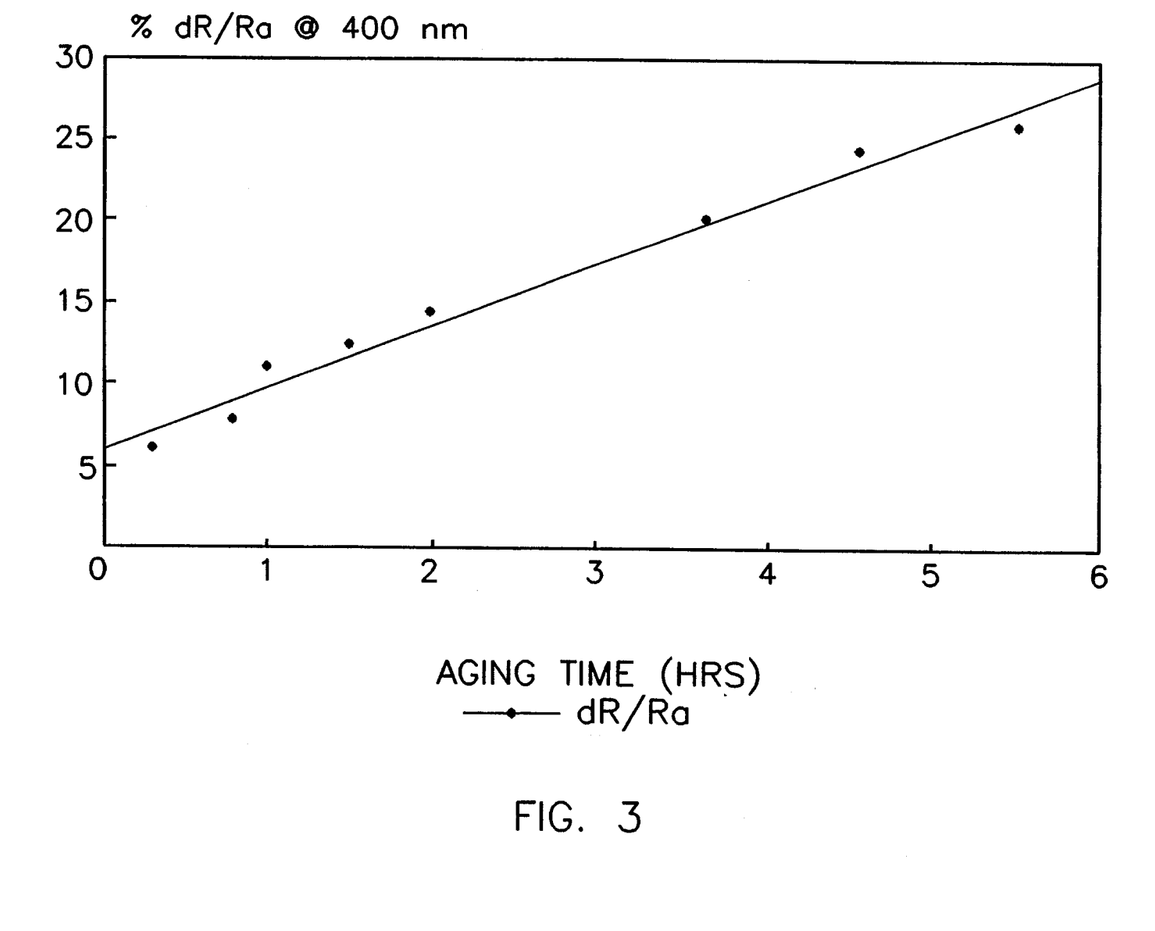
FIG. 3 is a plot of $dR/R_a$ (at a wavelength of 400 nm) vs. aging time for the chromate coated samples.

FIG. 3 is a plot of $dR/R_a$ at a wavelength of 400 nm vs. the aging time for the chromate coated PWB samples. It is plotted from data taken from FIG. 2 at 400 nm. 400 nm was chosen because it was a wavelength indicative of one of the characteristic peaks for $Cu_2O$. The curve shows how $dR/R_a$ increases with sample aging time.

Figure 4:
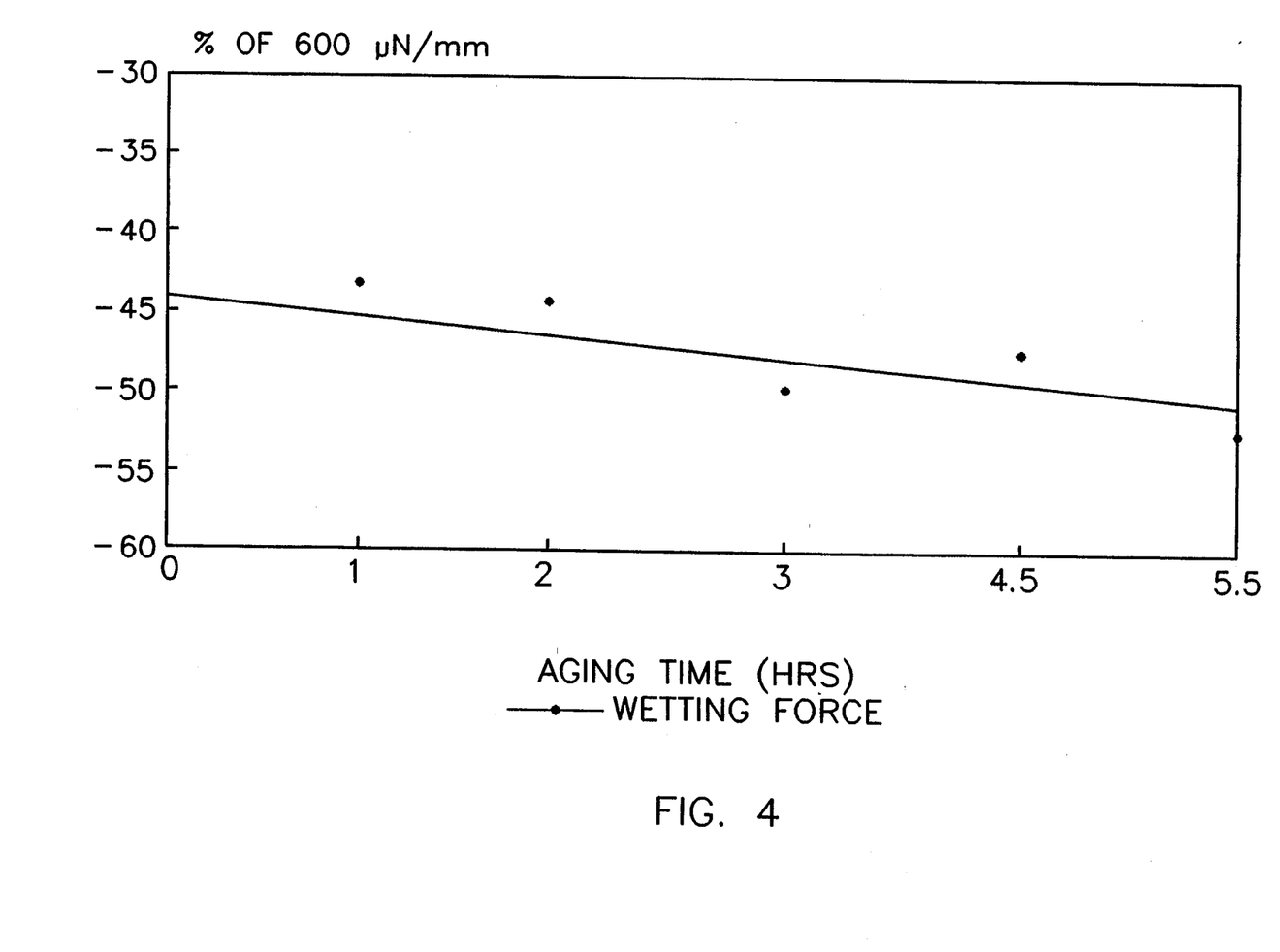
FIG. 4 is a plot of average wetting force (% of 600 um/mm) at t=2 seconds vs. aging time for chromate coated samples (experimental data).

FIG. 4 is a plot of average wetting force (% of 600 um/mm) at t=2 seconds from a wetting balance test vs. aging time for chromate coated copper foil samples. The curve shows that the average wetting force decreased with increased aging time which would indicate a degradation in solderability.

Figure 5:
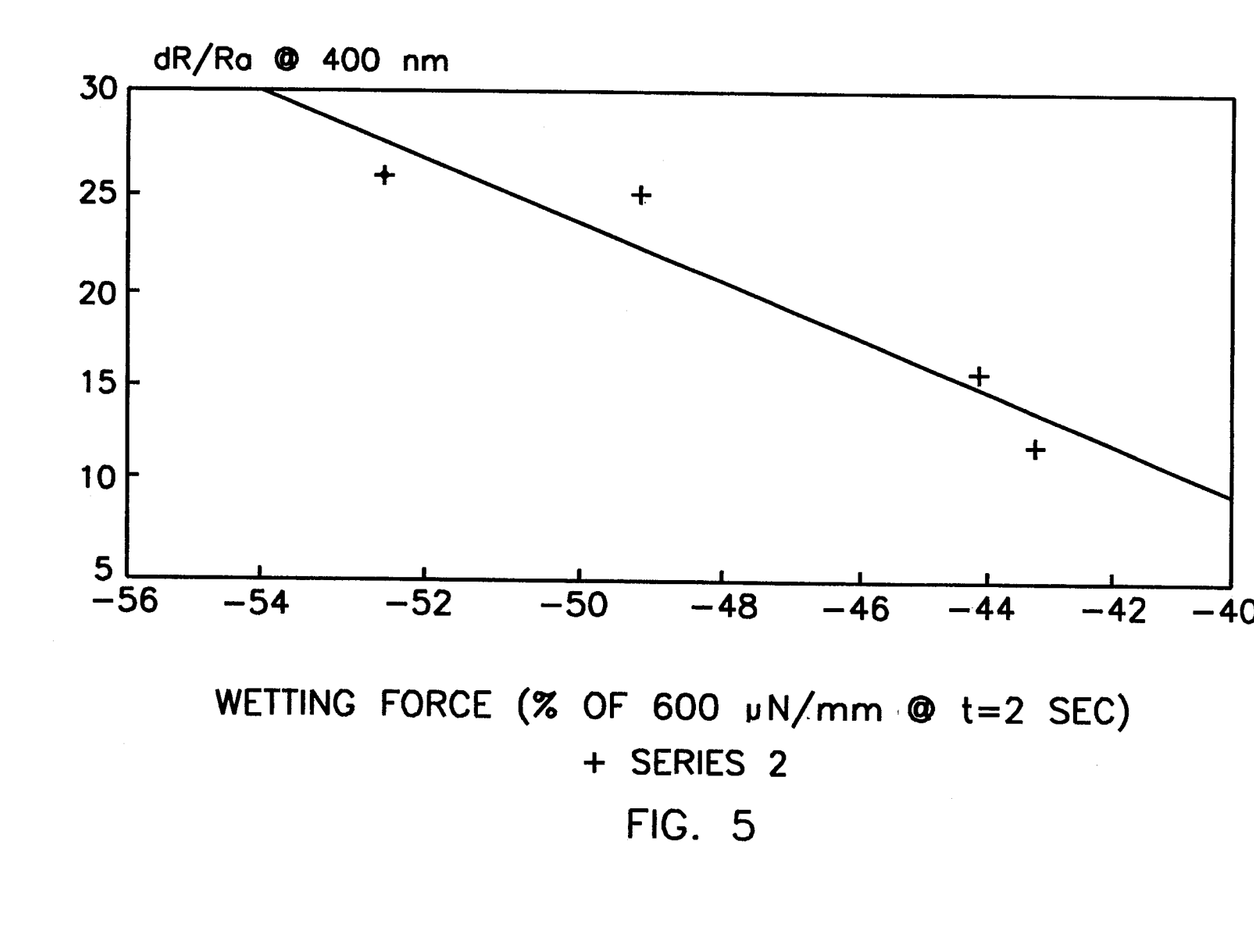
FIG. 5 combines FIGS. 3 and 4 and is a plot of $dR/R_a$ at 400 nm vs. the average wetting force at t=2 seconds.

FIG. 5 combines FIGS. 3 and 4 into a plot of $dR/R_a$ at 400 nm vs. average wetting force at t=2 seconds for samples at a given aging time. The plot shows that as $dR/R_a$ increases, average wetting force decreases. Therefore, $dR/R_a$ is related to the degradation in solderability of the samples and could be used as a gauge of solderability.

Figure 6:
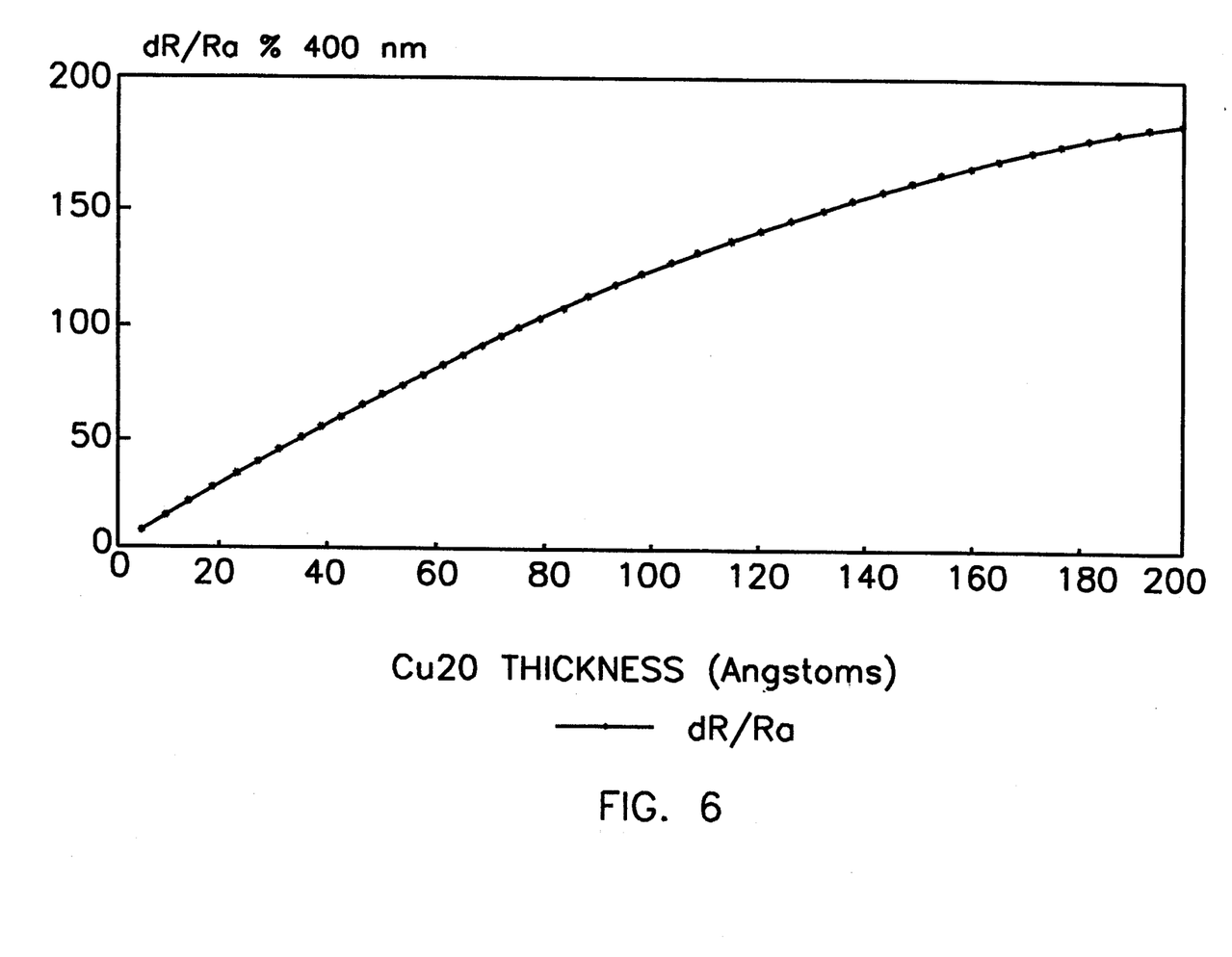
FIG. 6 is a calculated plot of the value of $dR/R_a$ vs. thickness of the oxide layer from the reflectivity equations.

FIG. 6 is a calculated curve of the ratio $dR/R_a$ to the oxide thickness for $Cu_2O$. It is calculated by knowing the index of refraction and index of absorption constants of the base metal and the oxide at a given wavelength and using the following equations for metals with corrosion films:

$$R_2 = \frac{(g_1^2 + h_1^2)e^{-2\alpha} + (g_2^2 + h_2^2)e^{-2\alpha} + A\cos2\phi + B\sin2\phi}{e^{2\alpha} + (g_1^2 + h_1^2)(g_2^2 + h_2^2)e^{-2\alpha} + C\cos2\phi + D\sin2\phi}$$

$$g_1 = \frac{n_0^2 - n_1^2 - k_1^2}{(n_0 + n_1)^2 + k_1^2}$$

$$h_1 = \frac{2n_0 k_1}{(n_0 + n_1)^2 + k_1^2}$$

$$g_2 = \frac{n_1^2 - n_2^2 + k_1^2 - k_2^2}{(n_1 + n_2)^2 + (k_1 + k_2)^2}$$

$$h_2 = \frac{2(n_1 k_2 - n_2 k_1)}{(n_1 + n_2)^2 + (k_1 + k_2)^2}$$

$$\alpha = \frac{2(\pi)(k_1)(d)}{\text{wavelength}} \text{ [radians]}$$

$$\phi = \frac{2(\pi)(n_1)(d)}{\text{wavelength}} \text{ [radians]}$$

where
 $n_1$ = index of refraction of thin film corrosion
 $k_1$ = index of absorption of thin film corrosion
 $d$ = thickness of thin film corrosion
(wherein the thin film corrosion is $Cu_2O$)
 $n_2$ = index of refraction of metal substrate
 $k_2$ = index of absorption of metal substrate
 $n_0$ = index of refraction of surrounding medium
(wherein the surrounding medium is air)

$$R_1 = \frac{(n_2 - n_0)^2 + k_2^2}{(n_2 + n_0)^2 + k_2^2} \text{ ; wherein } R_1 = \text{the reflectivity}$$

$$dR/R_a = \frac{R_1 - R_2}{(R_1 + R_2)/2} = \text{normalized difference in reflectivity}$$

These equations/relationships are well known to one having ordinary skill in the art. They are also set forth in C. W. Shanley et al. in "Differential Reflectometry—A New Optical Technique to Study Corrosion Phenomena," *Corrosion Science*, Vol. 20, page 467 (1980).

Figure 7:
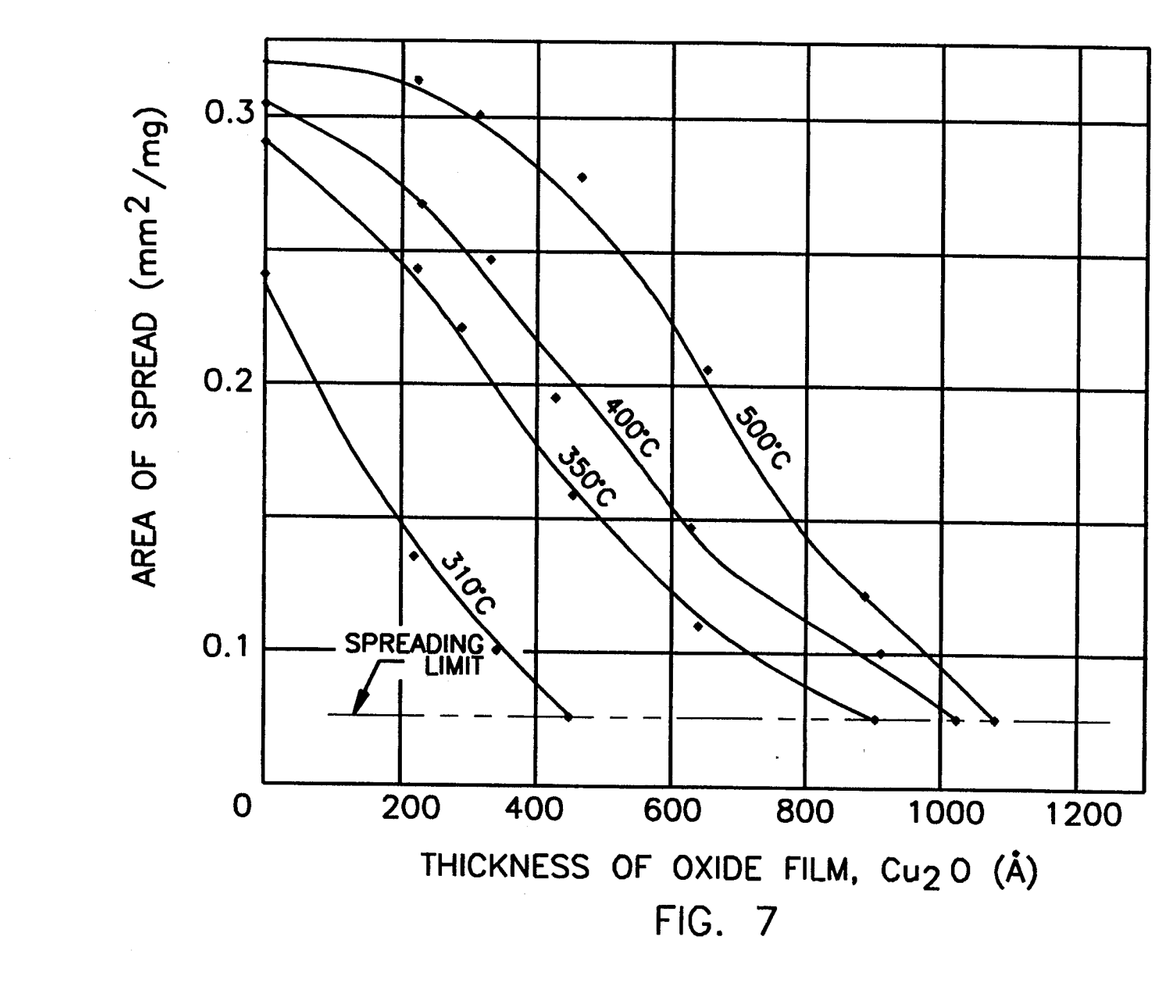
FIG. 7 is a plot of the wettability of copper by pure tin as a function of oxide thickness, see Ichiro Kawakatsu, "Wettability of Liquid Tin on Solid Copper," *Transactions of the Japan Institute of Metals*, Vol. 14, 114–119 (March, 1973).

FIG. 7 illustrates the wettability of pure copper by pure tin as a function of oxide thickness. FIGS. 6 and 7 show how this method can be used for systems other than the chromate coating—60/40 solder system. First one could use FIG. 1 to obtain a value of the ratio $dR/R_a$ at 400 nm for aged pure copper. Then from FIG. 6, one could get the oxide thickness for that sample. Then one could use FIG. 7 to get the solderability of the sample when using a 100% tin solder. The same process could be used for a number of different base metals or coatings such as copper, chromate coatings, tin coatings, solder coatings, or other like materials along with a variety of solder compositions. The process would be the same but the curves would have different peaks and general shapes.

Figure 8:
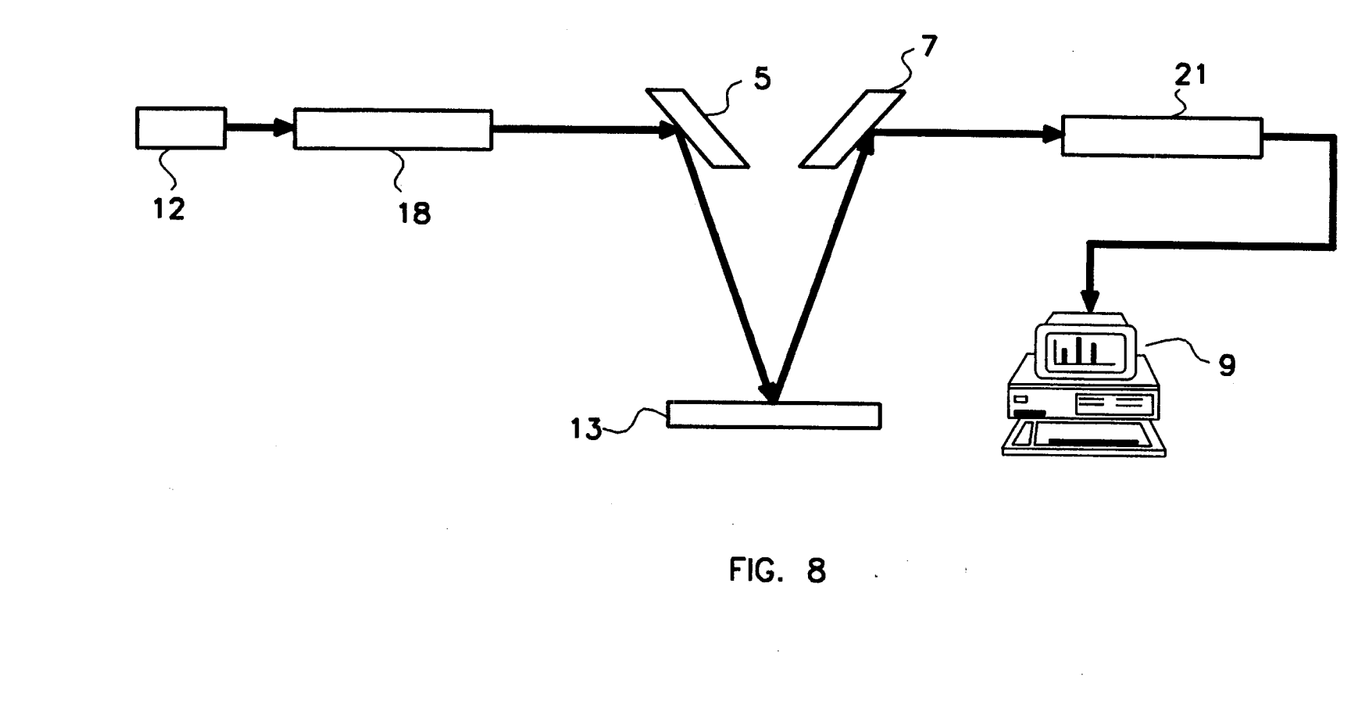
FIG. 8 is a schematic diagram of the type of differential reflectometer and how it may be used within the scope of the present invention.

FIG. 8 illustrates a differential reflectometer of the type which may be used and how it may be employed within the scope of the present invention. The present invention, solderability tester, uses a light source 12, which may be an unpolarized, white light source. The light emitted from said light source 12 passes through a monochromator 18 and reflects through a set of aiming mirrors 5 onto the component samples 13 to be analyzed. The light reflected from the component samples 13 is then directed through another set of aiming mirrors 7 which cause the light to be directed to a photomultiplier 21. Said photomultiplier 21 is connected to a conventional computer 9. The signal from the photomultiplier 21 is then processed by computer 9 to calculate the change in reflectance (dR) and the average reflectance ($R_a$) between the sample component 13 and a standard reference. Said standard reference of reflectance may be programmed into the computer 9. Data obtained at this point, if plotted against a range of wavelengths of light (i.e., 200–800 nm), will identify the type of oxide(s) present on the sample component 13. The computer 9 will then use correlations similar to FIG. 5 or FIGS. 6 and 7 to gauge the solderability of the sample component 13.

The present invention which is directed to a novel and unobvious procedure for evaluating the solderability of a sample, is fast, efficient and passive (non-destructive).

The embodiment set forth in the figures are merely illustrative of the present invention. It will be obvious to those skilled in the art that changes and modifications may be made to the solderability testing method herein without departing from the spirit of this invention.

SPECIFIC EMBODIMENT

A copper test sample circuit board (GEN0625C1/00 IAW MIL-P-13949F), manufactured by Polyclad of Franklin, NH, was cut up into test samples, was treated with Isoprep[R] 201 copper brightener (chromate treatment manufactured by Witco (Allied-Kelite Division), Melrose Park, IL) and was aged at 80° C. for various lengths of time. The copper brightener used is a chromate based composition. The samples were monitored for oxide growth using the differential reflectometry set-up shown in C. W. Shanley, "Differential Reflectometry—A New Optical Technique to Study Corrosion Phenomena," Vol. 20, *Corrosion Science* (1980).

A model 613 XENON light source manufactured by McPherson of Acton, Mass. was used as the light source. To this, a McPherson 0.3 meter scanning monochromator was connected to vary the wavelengths of the light from 0.2 to 0.8 nm. The light was then reflected from the sample to a photomultiplier manufactured by Thorn EMI Electron Tubes of Fairfield, N.J. The signal from the photomultiplier was then fed through a conventional differential amplifier and oscilloscope to a Hewlett-Packard Model 7047a X-Y recorder. The differential reflectogram from a series of these aged samples showed a definite trend of cuprous oxide growth when compared to differential reflectograms for cuprous oxide on pure copper.

Copper foil of the same type used on the test PWB samples was chromate treated with Isoprep 201 and cut into test samples of the same size as the PWB samples and aged at 80° C.

The copper foil samples were then tested on a Multicore Universal Solderability Tester which was connected to a Northgate personal computer running Perfect Balance software from National Standard Company in Niles, Mich. The samples were then tested using a rosin flux from Multicore. This data is plotted in FIG. 4.

Then the correlation between the differential reflection data and the wetting balance data was done by plotting $dR/R_a$ vs. wetting force for each aging time (see FIG. 5).

Also, knowing the derived relationship between reflectance and oxide thickness and that between oxide thickness and wettability/solderability, one is then equipped with a means for gauging the solderability of a part (see FIGS. 6 and 7). The lower the thickness of an oxide layer, the greater the solderability of the evaluated substrate. Stated differently, the thicker the oxide layer, the lesser the solderability of the same.

While particular embodiments of the present invention have been discussed, shown and described, it will be obvious to those skilled in the art that changes and modifications may be made without departing from this invention. Therefore, it is intended that the claims herein are to include all such obvious changes and modifications as fall within the true spirit of this invention.

We claim:

1. A method for evaluating the solderability of various substrates in a passive, non-destructive manner comprising
    evaluating a substrate for which solderability is to be determined using a differential reflectometer to determine the reflectance of said substrate;
    using this reflectance measurement to determine the type of, thickness of or presence of an oxide layer on said substrate; and
    correlating said oxide layer thickness or presence determination to the solderability properties of said substrate.

2. A method as set forth in claim 1, wherein said substrate is a printed circuit board.

3. A method as set forth in claim 1, wherein said substrate is composed of copper, nickel, palladium, tin or solder.

4. A method as set forth in claim 1, wherein said oxide layer thickness or presence determination is correlated using the relationship of the change in reflectance (dR) and the average reflectance ($R_a$) between said substrate and a reference substrate over a set range of light wavelengths.

5. A method as set forth in claim 4, wherein said set range of light wavelengths ranges from approximately 200 nm to 800 nm.

6. A method as set forth in claim 4, wherein the solderability of said substrate increases as the relationship of the ratio of $dR/R_a$ decreases.

7. A method for evaluating the solderability of various substrates in a passive, non-destructive manner comprising
   evaluating a substrate for which solderability is to be determined using a differential reflectometer to determine the reflectance of said substrate; and
   correlating said reflectance measurement to the solderability properties of said substrate.

8. A method as set forth in claim 7, wherein said substrate is a printed circuit board.

9. A method as set forth in claim 7, wherein said substrate is composed of copper, nickel, palladium, tin or solder.

10. A method as set forth in claim 7, wherein said reflectance measurement is correlated using the relationship of the change in reflectance (dR) and the average reflectance ($R_a$) between said substrate and a reference substrate over a set range of light wavelengths.

11. A method as set forth in claim 10, wherein said set range of light wavelengths ranges from approximately 200 nm to 800 nm.

12. A method as set forth in claim 10, wherein the solderability of said substrate increases as the relationship of the ratio of $dR/R_a$ decreases.

* * * * *